(12) United States Patent
Ouchi et al.

(10) Patent No.: US 8,559,594 B2
(45) Date of Patent: Oct. 15, 2013

(54) IMAGING APPARATUS AND IMAGING METHOD

(75) Inventors: Chidane Ouchi, Utsunomiya (JP); Kentaro Nagai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 380 days.

(21) Appl. No.: 13/085,199

(22) Filed: Apr. 12, 2011

(65) Prior Publication Data

US 2011/0200168 A1 Aug. 18, 2011

Related U.S. Application Data

(63) Continuation-in-part of application No. 12/842,937, filed on Jul. 23, 2010, now Pat. No. 8,009,797, which is a continuation of application No. PCT/JP2009/068434, filed on Oct. 27, 2009.

(30) Foreign Application Priority Data

Oct. 29, 2008 (JP) .................................. 2008-278425
Apr. 12, 2010 (JP) .................................. 2010-091562

(51) Int. Cl.
*G03H 5/00* (2006.01)
(52) U.S. Cl.
USPC ............................................. 378/36; 378/62
(58) Field of Classification Search
USPC .................................. 378/36, 62, 82
See application file for complete search history.

(56) References Cited

U.S. PATENT DOCUMENTS

| | | | |
|---|---|---|---|
| 5,812,629 | A | 9/1998 | Clauser |
| 2005/0117699 | A1 | 6/2005 | Yoneyama |
| 2005/0286680 | A1 | 12/2005 | Momose |

FOREIGN PATENT DOCUMENTS

| | | |
|---|---|---|
| CN | 1523448 A | 8/2004 |
| CN | 101013613 A | 8/2007 |
| DE | 102006037257 A1 | 8/2007 |
| JP | 2003-090807 A | 3/2003 |
| JP | 2005-152500 A | 6/2005 |
| JP | 2008-026098 A | 2/2008 |
| JP | 2008-200359 A | 9/2008 |
| JP | 2008-200360 A | 9/2008 |
| JP | 2009-244260 A | 10/2009 |
| WO | 2004-058070 A1 | 7/2004 |

OTHER PUBLICATIONS

Jiang et al., "X-ray Phase-Contrast Imaging with Three 2D Gratings" International Journal of Biomedical Imaging, 2007, pp. 1-8, vol. 2008, Hindawi Publishing Corporation.

Chen Bo, "Related Optical Problem Research on X-Ray phase contrast imaging," China Doctoral Dissertations Full-text Database, fundamental science edition issue 3, published Sep. 15, 2007; 120 pages (English Abstract pp. 4-5).

Takeda et al., "Fourier-Transform Method of Fringe-Pattern Analysis for Computer-Based Topography and Interferometry," J. Opt. Soc. Am., vol. 72, Jan. 1982, pp. 156-160.

*Primary Examiner* — Courtney Thomas
(74) *Attorney, Agent, or Firm* — Canon U.S.A., Inc. IP Division

(57) ABSTRACT

An imaging apparatus analyzes a periodic pattern of a Moiré due to Talbot interference by the Fourier transform method and forms an image. The imaging apparatus includes a first grating having a structure that transmits light beams from a beam source to refract or diffract the light beams and forms a self image based on a first periodic pattern by the Talbot interference at a predetermined position; a second grating that absorbs part of the first periodic pattern and causes a Moiré to be generated based on a second periodic pattern when the second grating is arranged at a position at which the self image is formed. All cross sections of the Moiré with axes in differential directions of a wavefront for the analysis by the Fourier transform method have a two-dimensional periodic structure in which periods of patterns in the second periodic pattern are the same.

12 Claims, 17 Drawing Sheets

☐ PORTION AS REFERENCE FOR PHASE
▨ PORTION WITH π-PHASE RELATIVELY CHANGED FROM REFERENCE

☐ PORTION AS REFERENCE FOR PHASE
▒ PORTION WITH π/2-PHASE RELATIVELY CHANGED FROM REFERENCE

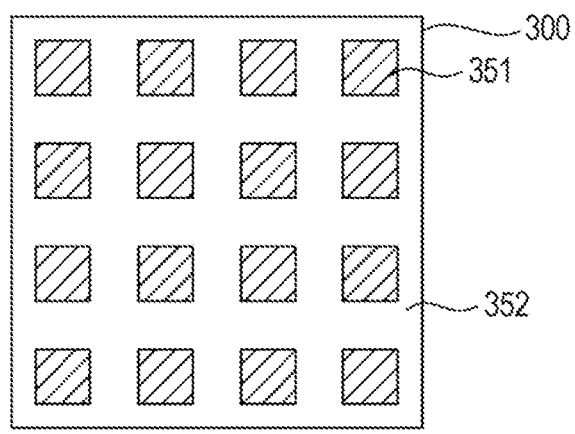
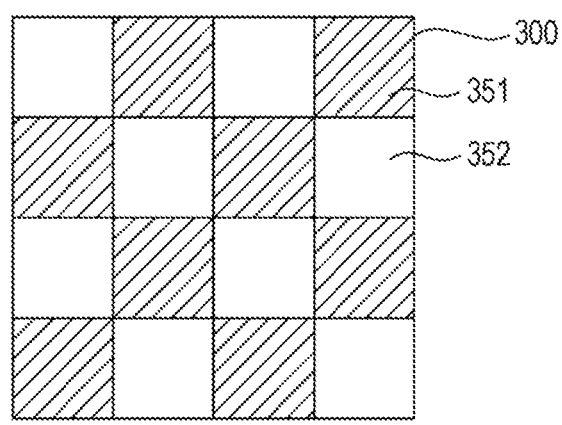

IMAGING APPARATUS AND IMAGING METHOD

CROSS REFERENCE TO RELATED APPLICATIONS

This application is a Continuation-in-part (CIP) of prior U.S. patent application Ser. No.: 12/842937 filed Jul. 23, 2010, which is a continuation of International Patent Application No. PCT/JP2009/068434 filed Oct. 27, 2009, the disclosures of which are hereby incorporated by reference herein in their entirety.

BACKGROUND OF THE INVENTION

1. Field of the Invention

The present invention relates to imaging apparatuses and imaging methods, and more particularly relates to an imaging apparatus and an imaging method that forms an image of a subject by using Talbot interference.

2. Description of the Related Art

Imaging techniques that use interference of light with various wavelengths including visible light and X-rays have been known.

Known one of such imaging methods may be a Talbot interference method.

The Talbot interference method will be briefly described below. When a subject is irradiated with light, the phase of the light is changed when the light is transmitted through the subject. When this light is emitted on a first grating (diffraction grating) having a specific pattern, the light diffracted by the first grating makes interference at a constant distance and forms an interference pattern called self image. When the self image is analyzed, information relating to the phase of the subject can be obtained.

Also, referring to the specification of U.S. Pat. No. 5,812,629, a shield grating including shielding portions that shield light and transmissive portions that transmit light is arranged at a position at which a self image is formed. By shielding part of the self image, a Moiré is formed.

If the described method, in which the Moiré is formed by using the self image and the Moiré is detected, is used, information relating to the phase of the subject can be obtained by using a detector with a resolution larger than the period of the self image.

Typically, when X-rays are used as light, the period of the self image is smaller than the resolution of the detector. Hence, the method of forming the Moiré is particularly effective when the X-rays are used as the light as described in U.S. Pat. No. 5,812,629. In an imaging apparatus described in U.S. Pat. No. 5,812,629, a second grating (shield grating) including the shielding portions that shield the light and the transmissive portions that transmit the light is arranged at the position at which the self image is formed. By shielding part of the self image, the Moiré is formed.

Several kinds of methods exist for generating the Moiré by using the second grating.

For example, there is a method of using a second grating having the same shape and period as the shape and period of the self image. By slightly rotating the angle of the second grating, a Moiré with high legibility is obtained.

For another example, there is a method of using a second grating having a period slightly different from the period of the self image. In either case, the self image is enhanced by the Moiré.

Also, several kinds of methods exist for calculating a change in wavefront shape of light due to a subject, from a displacement of a Moiré.

One of such methods is a method of analyzing the period of a Moiré by using a wave number space. Specifically, the Fourier transform and wavelet transform may be exemplified. It is to be noted that the Fourier transform contains the Fourier transform with a window function in this specification. M. Takeda, H. Ina, and S. Kobayashi, J. Opt. Soc. Am. 72, 156-160 (1982) describes a method of performing the Fourier transform for a Moiré by using the Fourier transform method, and extracting and analyzing a Moiré component in the wave number space. The principle of this method will be briefly described below. First, spatial frequency spectra are obtained by performing the Fourier transform for the detection result. Next, a spectrum with the frequency of a basic period component of the Moiré (hereinafter, referred to as carrier frequency) and an area around that spectrum are extracted, and are moved to an origin. The inverse Fourier transform is performed for this frequency spectrum to obtain a differential phase image of the subject, and the differential phase image is integrated to obtain a phase image of the subject.

The technique disclosed by M. Takeda, H. Ina, and S. Kobayashi, J. Opt. Soc. Am. 72, 156-160 (1982) is the one-dimensional Fourier transform method. With this transform method, a two-dimensional differential phase image cannot be obtained.

Owing to this, a first grating having a two-dimensional structure is used in a Talbot interferometer, to form a self image having a two-dimensional pattern. Then, a second grating having a proper shape corresponding to the self image is provided, and hence a two-dimensional Moiré can appear.

However, if the period of the Moiré is analyzed by using the wave number space, the accuracy for retrieval of the phase of light may vary depending on the shape of the Moiré.

In particular, when the phase is retrieved by the method of analyzing the period of the Moiré by using the wave number space, a satisfactory result may not be obtained depending on the combination of the first and second gratings.

SUMMARY OF THE INVENTION

Therefore, it is important to form the Moiré that is suitable for the analyzing method using the wave number space, by the combination of the first and second gratings.

The present invention provides an imaging apparatus and an imaging method capable of performing analysis with a high resolution when a period of a Moiré due to Talbot interference is analyzed by using a wave number space.

According to an aspect of the present invention, an imaging apparatus includes a first grating configured to form a two-dimensional interference pattern by diffracting light from a light source; a second grating including two-dimensionally arrayed shielding portions that shield the light and transmissive portions that transmit the light, and configured to shield part of the interference pattern; a detector configured to detect the light transmitted through the second grating; and an arithmetic unit configured to calculate a phase image or a differential phase image of a subject based on a periodic pattern of an intensity distribution of the light detected by the detector. The first and second gratings are configured such that a period of the intensity distribution in a first direction becomes equivalent in an entire region on a detection surface of the detector.

Further features of the present invention will become apparent from the following description of exemplary embodiments with reference to the attached drawings.

BRIEF DESCRIPTION OF THE DRAWINGS

FIG. 18A illustrates a two-dimensional absorption grating relating to the embodiment.

FIG. 18B illustrates a two-dimensional absorption grating relating to the embodiment.

DESCRIPTION OF THE EMBODIMENTS

Embodiments of the present invention will be described below in detail with reference to the accompanying drawings.

An imaging apparatus according to this embodiment uses X-rays with wavelengths of 10 nm or smaller as light. The imaging apparatus analyzes a periodic pattern of a Moiré due to Talbot interference by the Fourier transform method, and obtains a phase image or a differential phase image of a subject.

Figure 1:
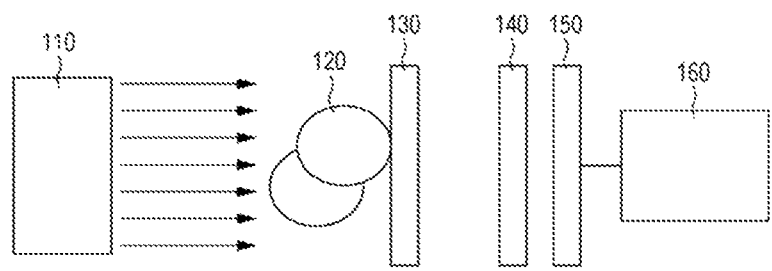
FIG. 1 illustrates a configuration of an X-ray phase imaging apparatus relating to an embodiment of the present invention.

FIG. 1 illustrates an imaging apparatus that is used in this embodiment.

The imaging apparatus of this embodiment includes an X-ray source 110 that radiates spatially coherent X-rays, a first grating 130 that diffracts the X-rays, a second grating 140 having two-dimensionally periodically arrayed shielding portions that shield the X-rays and transmissive portions that transmit the X-rays, a detector 150 that detects an intensity distribution of the X-rays transmitted through the second grating 140, and an arithmetic unit 160 that analyzes the detection result.

The imaging apparatus of this embodiment includes the X-ray source 110 as a light source. When the X-rays emitted from the X-ray source 110 are transmitted through a subject 120, the phase of the X-rays is changed in accordance with the refractive index and shape of the subject 120. In FIG. 1, the subject 120 is arranged between the X-ray source 110 and the first grating 130. However, the subject 120 may be arranged between the first grating 130 and the second grating 140.

The first grating 130 is a transmissive diffraction grating called phase grating. In the first grating 130, portions having two kinds of transmission characteristics are arranged to have a two-dimensional periodic structure. Hence, the X-rays transmitted through the first grating 130 form a self image in which bright sections and dark sections are two-dimensionally periodically arrayed at a constant interval.

Figure 2A:
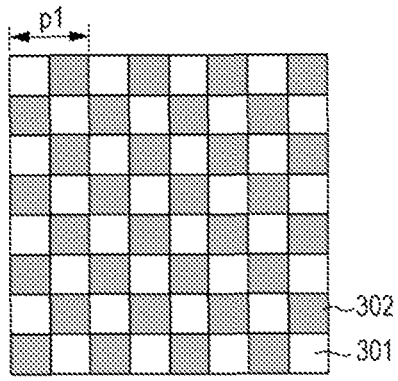
FIG. 2A illustrates a first grating relating to the embodiment.

FIG. 2A illustrates the first grating 130 that is used in this embodiment. It is to be noted that FIG. 2A shows part of the first grating 130 in an enlarged manner.

Figure 2B:
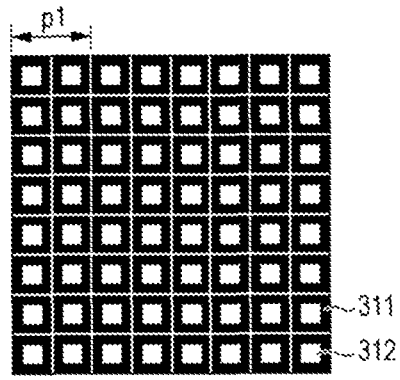
FIG. 2B illustrates a self image relating to the embodiment.

FIG. 2A illustrates a grating ($\pi$ grating) configured to shift the phase of the X-rays transmitted through first regions 301 relative to the phase of the X-rays transmitted through second regions 302 by $\pi$. FIG. 2B illustrates a self image that is formed when the phase grating shown in FIG. 2A is used. The self image includes dark sections 311 and bright sections 312 that are arranged in a lattice-shaped pattern with a period p1. This self image has a two-dimensional period.

It is to be noted that the self image shown in FIG. 2B is a self image when the subject 120 is not arranged between the X-ray source 110 and the first grating 130. Hereinafter, when the shape of the self image is described in this specification, unless otherwise noted, the self image is a self image that is formed when the subject is not arranged between the X-ray source and the first grating. In this embodiment, the self image shown in FIG. 2B is formed by using the first grating 130 shown in FIG. 2A; however, the first grating used for the present invention is not limited thereto, and the self image formed by the first grating is not limited thereto neither.

When phase imaging by using X-rays is performed, the period of the first grating 130 becomes about several micrometers.

This is because, when d is a period of a first grating and λ is a wavelength of incident light, a basic distance z called Talbot distance is given by Expression 1 as follows:

$$z = d^2/2\lambda \qquad (1).$$

In fact, various coefficients are applied to Expression 1 in accordance with the shape of the first grating 130 and a desired contrast.

With reference to Expression 1, assuming that the distance between the first grating 130 and the self image is the size of the apparatus and is about several tens of centimeters, it is found that the grating period of the first grating 130 has to be an order of magnitude of about several micrometers.

As the result, the period of the self image becomes about several micrometers. A typically used X-ray detector has a resolution of about several tens of micrometers at the most. There is a difference between this resolution and the period of the self image. The self image cannot be formed in the current situation. Hence, the imaging apparatus of this embodiment enhances the self image by using a Moiré.

Figure 3:
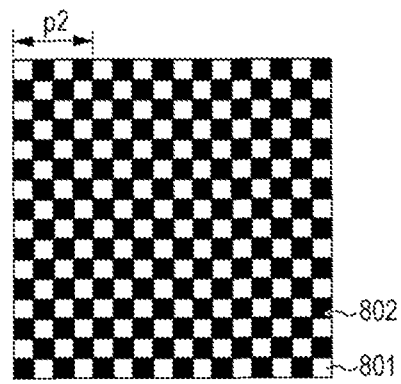
FIG. 3 illustrates a second grating relating to the embodiment.

In this embodiment, the second grating 140 is used to form the Moiré. FIG. 3 illustrates the second grating 140 in this embodiment. It is to be noted that FIG. 3 shows part of the second grating 140 in an enlarged manner.

The second grating 140 includes shielding portions 802 that shield the X-rays and transmissive portions 801 that transmit the X-rays. The shielding portions 802 and the transmissive portions 801 are arranged in a checker board designed pattern with a period p2. This second grating 140 two-dimensionally has a period. The period p2 of the second grating 140 is slightly different from the period p1 of the self image. Due to the difference between the periods, undulations of bright sections and dark sections, i.e., a Moiré is generated.

Figure 4A:
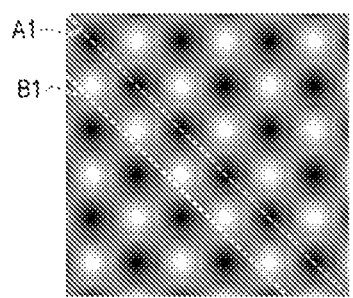
FIG. 4A illustrates a Moiré relating to the embodiment.

FIG. 4A illustrates a Moiré formed by using the first grating 130 shown in FIG. 2A and the second grating 140 shown in FIG. 3. The Moiré and the Fourier transform will be described later.

The Moiré shown in FIG. 4A is a Moiré when the subject 120 is not arranged between the X-ray source 110 and the first grating 130, or between the first grating 130 and the second grating 140. Hereinafter, when the shape of the Moiré is described in this specification, unless otherwise noted, the Moiré is formed when the subject is not arranged between the X-ray source and the first grating, or between the first grating and the second grating. Also, in this embodiment, the second grating 140 including the shielding portions 802 and the transmissive portions 801 arranged in a checker board designed pattern is used; however, the second grating used for the present invention is not limited thereto. Further, the shielding portions do not have to completely shield X-rays, and the transmissive portions do not have to completely transmit X-rays. It is to be noted that the shielding portions have to shield the X-rays and the transmissive portions have to transmit the X-rays by a certain degree so that a Moiré can be formed by superposing these portions on the self image.

The detector 150 is an imaging element (for example, charge-coupled device, CCD) that can detect the intensity of X-rays. The detector 150 detects the intensity distribution of X-rays transmitted through the second grating 140. In other words, the detector 150 detects a Moiré.

The intensity distribution of the X-rays detected by the detector 150 is analyzed by the arithmetic unit 160. In this embodiment, the phase image or the differential phase image of the subject is obtained by using the Fourier transform method with a window function (window Fourier transform). The window Fourier transform is processing that determines the phase by successively performing the Fourier transform while the Moiré is multiplied by a window function having a local value. This processing handles a large amount of data and hence takes a time. However, the phase can be retrieved more correctly and accurately as compared with that the phase is obtained by the Fourier transform method without the window function.

Here, the concept of the method of retrieving the phase by the Fourier transform will be briefly described.

FIGS. 14A to 14D illustrate the overview.

Figure 14A:
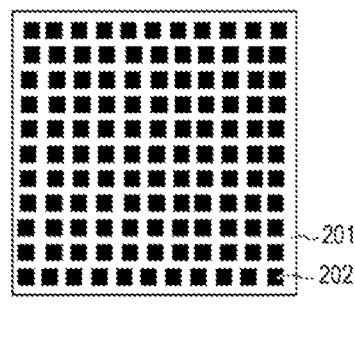
FIG. 14A illustrates an example of a phase retrieval process using the Fourier transform.

In the Fourier transform method, the Moiré is decomposed into Fourier components, and a specific frequency region is analyzed, to retrieve an image. FIG. 14A illustrates an example of a Moiré before the analysis.

A periodic Moiré 202 is formed in a screen 201. A position shift of the Moiré 202 represents information relating to a change in phase of X-rays due to a subject.

Figure 14B:
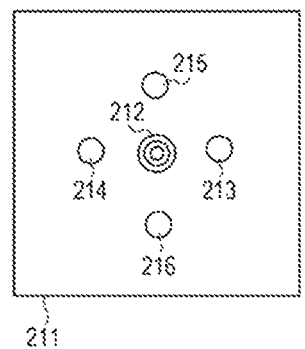
FIG. 14B illustrates the example of the phase retrieval process using the Fourier transform.

If the Moiré 202 is transformed in the entire screen 201; the result shown in FIG. 14B is obtained.

Here, the origin of the wave number space is the center of a screen 211. In the wave number space, a zeroth order spectrum 212 appears at the origin, and first order spectra 213, 214, 215, and 216 appear around the zeroth order spectrum 212.

The positions and number of spectra around the origin depend on the shape of a Moiré before the Fourier transform.

At least one of the spectra is used for the wavefront analysis. Typically, any of the first order spectra is used.

Figure 14C:
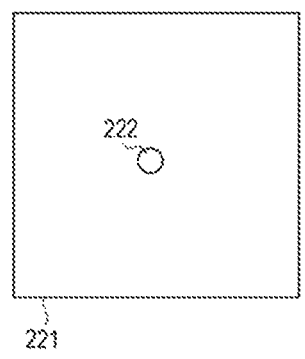
FIG. 14C illustrates the example of the phase retrieval process using the Fourier transform.

With the method described by M. Takeda, H. Ina, and S. Kobayashi, J. Opt. Soc. Am. 72, 156-160 (1982), one point of the first order spectra and an area around the point are cut and moved to an origin 222 in another wave number space 221 (FIG. 14C).

Figure 14D:
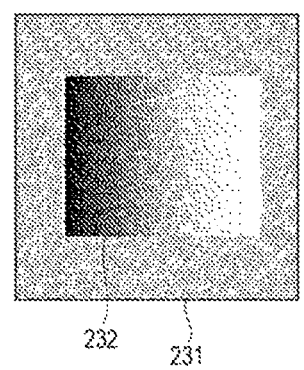
FIG. 14D illustrates the example of the phase retrieval process using the Fourier transform.

By performing the inverse Fourier transform, a differential image 232 of the subject can be obtained in an actual space 231 (FIG. 14D). The differential image 232 is integrated, and hence the wavefront is retrieved.

The above-described method is an example of the Fourier transform method. The present invention is not limited to such an analysis method, and may use another method.

For example, a plurality of spectrum points may be used for analyzing the wave number space further in detail.

Figure 4B:
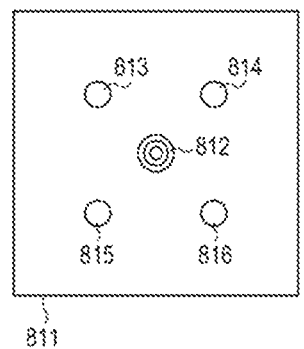
FIG. 4B is a schematic illustration obtained by performing the Fourier transform for the Moiré relating to the embodiment.

The analysis method of obtaining the phase image or differential phase image of the subject from the intensity distribution of the Moiré detected in this embodiment will be briefly described. FIG. 4B schematically illustrates the result obtained by performing the Fourier transform for the Moiré (FIG. 4A) in this embodiment in an entire detection surface of the detector 150.

In FIG. 4B, a zeroth order spectrum 812 is present at the center of a wave number space 811, and first order spectra 813, 814, 815, and 816 are present around the zeroth order spectrum 812.

If at least any one of the first order spectra is analyzed like the example shown in FIGS. 14A to 14D, a differential phase image of a subject is obtained. Also, if the differential phase image is integrated, a phase image of the subject is obtained.

Figure 4C:
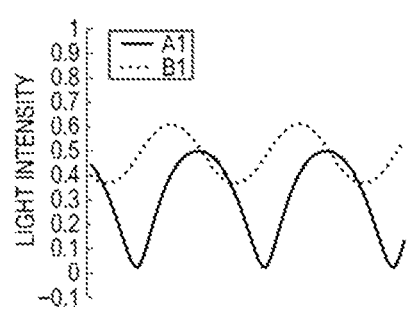
FIG. 4C illustrates intensity distributions of the Moiré relating to the embodiment.

FIG. 4C illustrates intensity distributions of X-rays along an axis A1 and an axis B1 of the Moiré shown in FIG. 4A. The intensity distribution along the axis A1 is indicated by a solid line, and the intensity distribution along the axis B1 is indicated by a broken line. The axis B1 is parallel to the axis A1. As shown in FIG. 4C, the intensity distribution along the axis A1 and the intensity distribution along the axis B1 have the same period although the intensity distributions have different shapes and amplitudes. Like the axis B1, the Moiré shown in FIG. 4A provides intensity distributions having the same period as the period of the intensity distribution along the axis A1 as long as the intensity distributions are along axes parallel to the axis A1.

In other words, assuming that a direction parallel to the axis A1 in FIG. 4A is a first direction, the Moiré shown in FIG. 4A provides intensity distributions having an equivalent period in the first direction in the entire region on the Moiré.

Also, the Moiré has a two-dimensional period, and hence an intensity distribution along an axis C1 (not shown in the drawing) that is perpendicular to the axis A1 is periodic. Like the axis A1, assuming that a direction parallel to the axis C1 is a second direction, the Moiré shown in FIG. 4A provides intensity distributions having an equivalent period in the second direction in the entire region on the Moiré.

It is to be noted that the entire region on the Moiré in this specification does not contain a region that is not used for the analysis using the wave number space (for example, the Fourier transform).

In the Fourier transform method, the periods of the X-ray intensity distributions in cross sections along differential directions have to be equivalent in order to correctly calculate a wavefront differential of X-rays. The shapes of the intensity distributions are desirably the shapes of sine waves.

Assuming that the direction parallel to the axis A1 in FIG. 4A is the first direction as described above, the Moiré shown in FIG. 4A provides the intensity distributions with the equivalent period in the first direction in the entire region on the Moiré. Also, assuming that the direction parallel to the axis C1 that is perpendicular to the axis A1 in FIG. 4A is the second direction, the Moiré shown in FIG. 4A provides intensity distributions with the equivalent period in the second direction in the entire region on the Moiré. Hence, assuming that the first and second directions are differential directions, the spectra of that period can be extracted by the Fourier transform from the entire region on the Moiré. Accordingly, a change in phase of X-rays due to a subject can be analyzed in more detail as compared with the case of the related art. Alternatively, the number of differential directions may be one. Even if the differential direction is the first or the second direction, a change in phase of X-rays due to a subject can be analyzed in more detail as compared with the case of the related art (with one differential direction).

Now, specific examples and a comparative example will be described.

Figure 13:
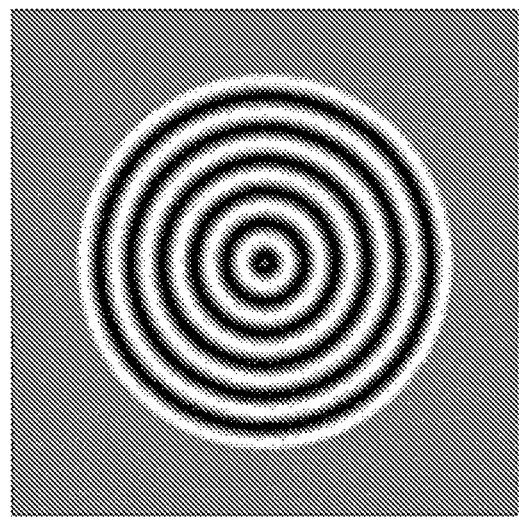
FIG. 13 illustrates a subject.

In each of the following examples and comparative example, a differential phase image, which is obtained when a subject is a circular pattern having a thickness of 40 micrometers and patterned on silicon as shown in FIG. 13, is calculated. Then, the examples are compared with the comparative example.

In the drawing, the height of the pattern is expressed by contrast.

First, the comparative example will be described.

COMPARATIVE EXAMPLE

The comparative example will be described with reference to FIGS. 15A to 15D.

An imaging apparatus in this comparative example is different in a second grating from the imaging apparatus described in the embodiment. Other configuration of this comparative example is the same as that of the embodiment.

Figure 15A:
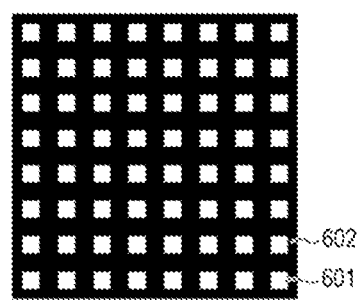
FIG. 15A illustrates a second grating relating to a comparative example.

The imaging apparatus according to this comparative example includes an X-ray source that emits parallel X-rays with 17.5 keV as a light source; a phase grating ($\pi$ grating) shown in FIG. 2A as a first grating; and a grating having a structure shown in FIG. 15A as a second grating. In addition, the imaging apparatus includes a detector and an arithmetic unit.

FIG. 15A schematically shows part of the shape of the second grating in an enlarged manner. The second grating in this comparative example includes a transmissive portion 601 that transmits incident X-rays, and shielding portions 602 that shield the incident X-rays. The second grating has a period slightly different from the period of the first grating. Due to the difference, a Moiré shown in FIG. 15B is generated.

Figure 15B:
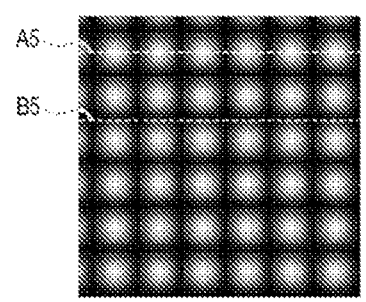
FIG. 15B illustrates a Moiré relating to the comparative example.
Figure 15C:
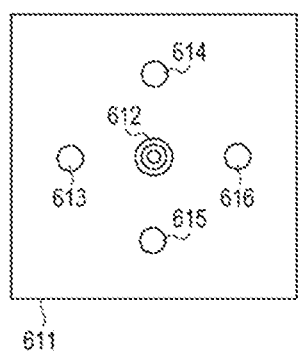
FIG. 15C is a schematic illustration obtained by performing the Fourier transform for the Moiré relating to the comparative example.

FIG. 15C schematically illustrates the result obtained by performing the Fourier transform for the Moiré shown in FIG. 15B.

Like FIG. 4B, a zeroth order spectrum 612 is present at the center of a wave number space 611, and first order spectra 613, 614, 615, and 616 are present around the zeroth order spectrum 612. Any spectrum of the first spectra is analyzed to calculate a differential phase image of the subject.

Figure 16:
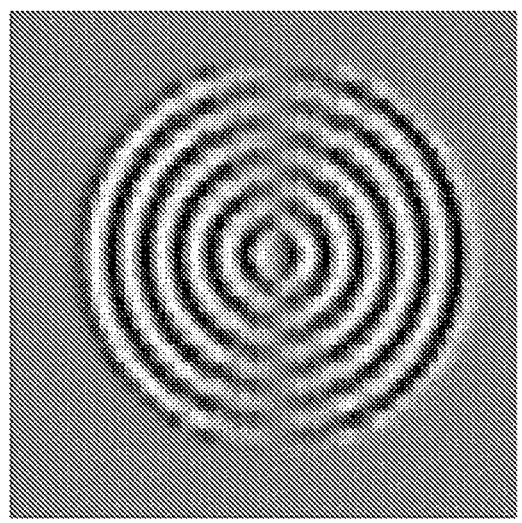
FIG. 16 illustrates the result of wavefront analysis according to the comparative example.

FIG. 16 is the differential phase image of the subject obtained in this comparative example.

This drawing illustrates the shape obtained by differentiating the subject in FIG. 13 in the x-axis (horizontal-axis) direction. The shape is entirely reproduced. However, if the shape is carefully observed, the shape has step-like noises (jaggies) although the shape is originally circular. The detailed shape is not reproduced.

This is because the shape of the Moiré obtained from the combination of the self image by the first grating and the second grating is not suitable for retrieval of a wave front.

Figure 15D:
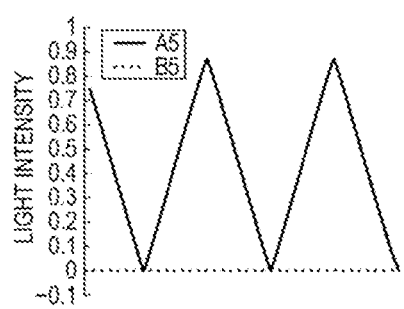
FIG. 15D illustrates an intensity distribution of the Moiré relating to the comparative example.

FIG. 15D illustrates intensity distributions of X-rays along an axis A5 and an axis B5 of the Moiré shown in FIG. 15A. The intensity distribution along the axis A5 is indicated by a solid line, and the intensity distribution along the axis B5 is indicated by a broken line. The axis B5 is parallel to the axis A5. As described above, in the Fourier transform method, the periods of the X-ray intensity distributions along the differential directions have to be equivalent.

As shown in FIG. 15D, the intensity distribution of the X-rays along the axis A5 has a shape of a triangular wave, and has a period that can be analyzed by using the Fourier transform. In contrast, the intensity distribution of the X-rays along the axis B5 is constantly zero. Information of a wavefront relating to the axis B5 is not obtained.

Therefore, the wavefront is not analyzed in detail, and step-like jaggies as shown in FIG. 16 entirely appear.

Example 1

Example 1 will be described with reference to FIGS. 4A to 4D.

Example 1 has the same configuration as the configuration of the imaging apparatus described in the embodiment, and is different from the comparative example in the second grating. In particular, the imaging apparatus according to this example includes the X-ray source that emits parallel X-rays with 17.5 keV as the light source; the phase grating shown in FIG. 2A as the first grating; and the grating having the structure shown in FIG. 3 as the second grating. In addition, the imaging apparatus includes the detector and the arithmetic unit.

As described above, the second grating has the period p2 that is slightly different from the period p1 of the first grating. Due to the difference, the Moiré shown in FIG. 4A is formed. FIG. 4B illustrates the result obtained by performing the Fourier transform for the Moiré. FIG. 4C illustrates the intensity distribution of the X-rays along the axis A1 on the Moiré by using the solid line, and the intensity distribution of the X-rays along the axis B1 by using the broken line.

Any one spectrum is selected from the first order spectra 813, 814, 815, and 816 shown in FIG. 4B and is analyzed to calculate a differential phase image of a subject.

Figure 5:
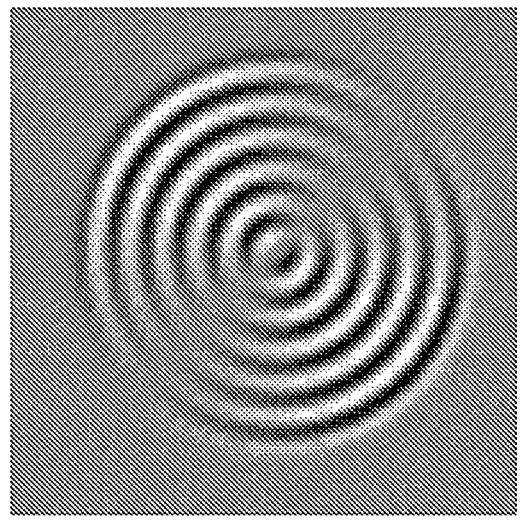
FIG. 5 illustrates the result of wavefront analysis according to the embodiment.

FIG. 5 illustrates the differential phase image obtained in this example.

When the example is compared with the comparative example, since the position of the first order spectrum is obliquely located at 45 degrees, the differential phase image is obliquely inclined at 45 degrees as compared with the differential phase image shown in FIG. 16. Otherwise, jaggies of edges are not noticeable as compared with the differential phase image shown in FIG. 16, and a detailed shape can be reproduced.

As described above, FIG. 4C illustrates the intensity distributions of the X-rays along the axes A1 and B1 of the Moiré shown in FIG. 4A. The intensity distribution along the axis A1 and the intensity distribution along the axis B1 have the slightly different shapes and amplitudes; however, these intensity distributions have the same period. Similarly to the axis B1, assuming that the direction parallel to the axis A1 in FIG. 4A is the first direction, the Moiré shown in FIG. 4A provides intensity distributions with the equivalent period in the first direction in the entire region on the Moiré.

Accordingly, the spectra with that period can be extracted by the Fourier transform, and the wavefront can be analyzed in detail. The more detailed shape can be analyzed as compared with the comparative example.

Example 2

For Example 2, an imaging apparatus that uses a second grating including semi-transmissive portions will be described with reference to FIGS. 6A to 6D. The imaging apparatus of Example 2 has a structure similar to the structure of Example 1 except for a second grating.

Figure 6A:
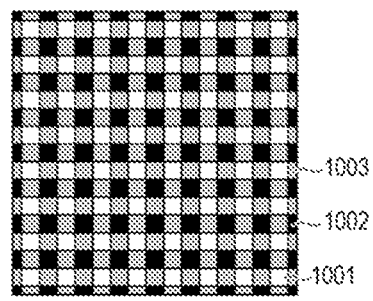
FIG. 6A illustrates a second grating relating to Example 2.
Figure 6B:
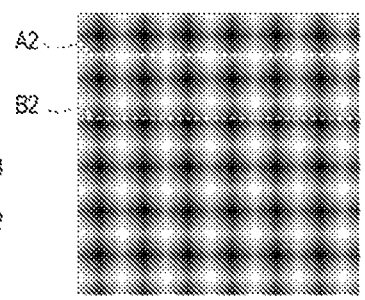
FIG. 6B illustrates a Moiré relating to Example 2.

FIG. 6A illustrates the second grating in this example. FIG. 6A schematically shows part of the shape of the second grating in an enlarged manner. Reference sign 1001 denotes transmissive portions, and 1002 denotes shielding portions for incident X-rays. In addition, the second grating used in this example includes semi-transmissive portions 1003 that transmit 50% of the incident X-rays. When the X-rays are transmitted through the semi-transmissive portions 1003 in this example, the intensity of the incident X-rays is halved, but the semi-transmissive portions 1003 are effective as long as the semi-transmissive portions 1003 transmit the X-rays more than the shielding portions 1002 do and shield the X-rays more than the transmissive portions 1001 do. In the second grating in this example, the shielding portions 1002, the transmissive portions 1001, and the semi-transmissive portions 1003 are respectively arrayed in checker board designed patterns as shown in FIG. 6A. Also, the shielding portions 1002, the transmissive portions 1001, and the semi-transmissive portions 1003 are arranged in a Bayer Array. Like Example 1, the second grating in this example has a period slightly different from the period of a self image. Due to the difference, a Moiré shown in FIG. 6B is formed. Like Example 1, FIG. 6C illustrates the result obtained by performing the Fourier transform for the Moiré, and FIG. 6D illustrates an intensity distribution of the X-rays along an axis A2 on the Moiré by using a solid line, and an intensity distribution of the X-rays along an axis B2 on the Moiré by using a broken line.

Figure 6C:
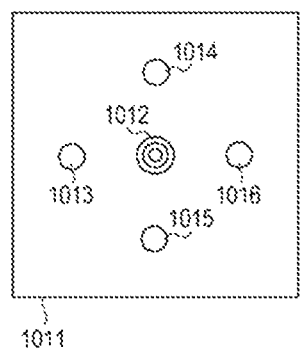
FIG. 6C is a schematic illustration obtained by performing the Fourier transform for the Moiré relating to Example 2.
Figure 6D:
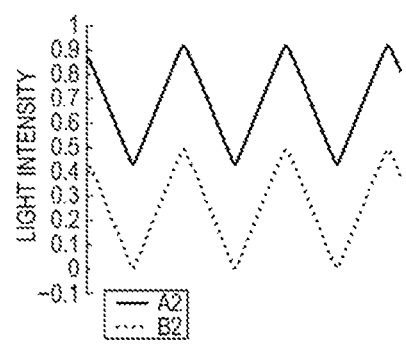
FIG. 6D illustrates intensity distributions of the Moiré relating to Example 2.

If the Fourier transform is performed for the Moiré shown in FIG. 6B, spectra shown in FIG. 6C appear. Like FIG. 4B, in FIG. 6C, a zeroth order spectrum 1012 is present at the center of a wave number space 1011, and first order spectra 1013, 1014, 1015, and 1016 are present around the zeroth order spectrum 1012.

Any one spectrum is selected from the first order spectra 1013, 1014, 1015, and 1016 shown in FIG. 6C and is analyzed to calculate a differential phase image of a subject.

Figure 7:
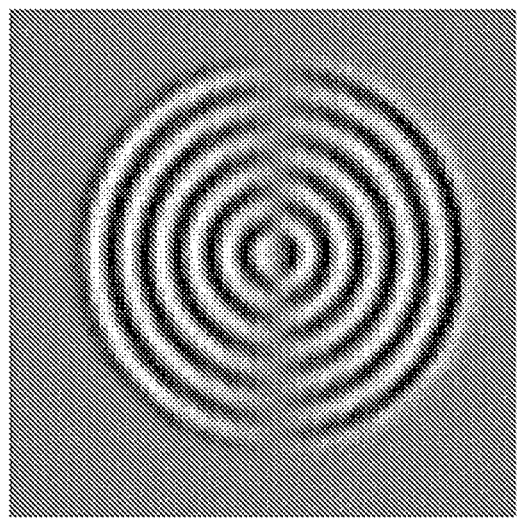
FIG. 7 illustrates the result of wavefront analysis according to Example 2.

FIG. 7 illustrates the differential phase image obtained in this example.

The first order spectra appears at the same position as the position in the comparative example. Jaggies of edges are not noticeable as compared with the differential phase image shown in FIG. 16, and a detailed shape can be reproduced.

FIG. 6D illustrates intensity distributions of the X-rays along the axes A2 and B2 of the Moiré shown in FIG. 6B. Like the Moiré shown in FIG. 4A, assuming that a direction parallel to the axis A2 is a first direction, the Moiré shown in FIG. 6B provides intensity distributions having an equivalent period in the first direction in the entire region on the Moiré. Accordingly, like Example 1, a detailed shape can be analyzed as compared with the comparative example. Unlike the Moiré shown in FIG. 4A, the Moiré along the axis B2 shown in FIG. 6B provides intensity distributions with equivalent amplitudes and shapes in the first direction. The same pattern is repeated with the same period in the entire region on the Moiré. Accordingly, the spectra with that period can be easily extracted by the Fourier transform.

Example 3

In Example 3, an imaging apparatus that forms a self image that is different from the self image of the imaging apparatus according to Example 1 will be described with reference to FIGS. 8A and 8B, and 9A to 9D. The imaging apparatus of Example 3 has a structure similar to the structure of Example 1 except for first and second gratings.

Figure 8A:
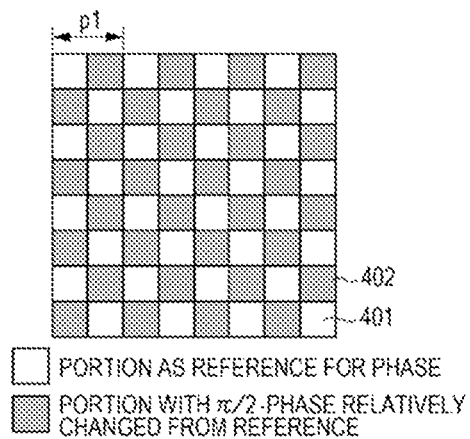
FIG. 8A illustrates a first grating relating to Example 3.

FIG. 8A shows the first grating used in this example. It is to be noted that FIG. 8A shows part of the first grating in an enlarged manner.

Figure 8B:
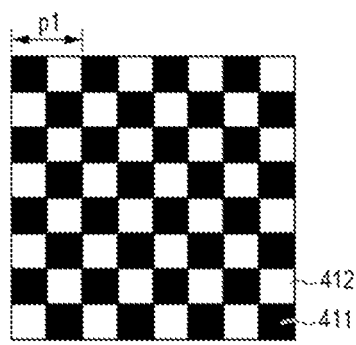
FIG. 8B illustrates a self image relating to Example 3.

FIG. 8A shows a grating ($\pi/2$ grating) configured to shift the phase of X-rays transmitted through first regions 401 relative to the phase of the X-rays transmitted through second regions 402 by $\pi/2$. Also, FIG. 8B shows a self image that is formed when the phase grating shown in FIG. 8A is used. The self image includes dark sections 411 and bright sections 412 that are arranged in a periodic checker board designed pattern with a period p1. This self image has a two-dimensional period.

Figure 9A:
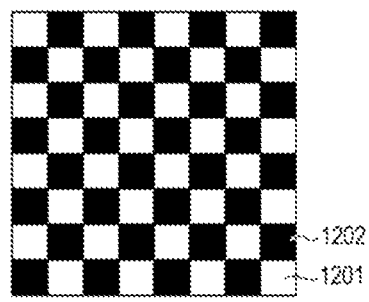
FIG. 9A illustrates a second grating relating to Example 3.
Figure 9B:
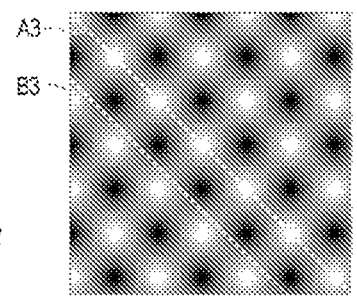
FIG. 9B illustrates a Moiré relating to Example 3.

FIG. 9A shows the second grating used in this example. It is to be noted that FIG. 9A schematically shows part of the second grating in an enlarged manner. The second grating used in this example includes transmissive portions 1201 that transmit the X-rays and shielding portions 1202 that shield the X-rays. The transmissive portions 1201 and the shielding portions 1202 are arranged in a checker board designed pattern. The second grating has a period slightly different from the period of the first grating. Due to the difference, a Moiré shown in FIG. 9B is generated. Like Example 1, FIG. 9C illustrates the result obtained by performing the Fourier transform for the Moiré, and FIG. 9D illustrates an intensity distribution of the X-rays along an axis A3 on the Moiré by using a solid line, and an intensity distribution of the X-rays along an axis B3 on the Moiré by using a broken line.

Figure 9C:
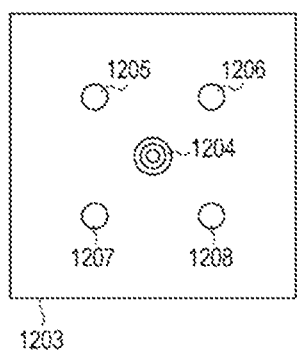
FIG. 9C is a schematic illustration obtained by performing the Fourier transform for the Moiré relating to Example 3.
Figure 9D:
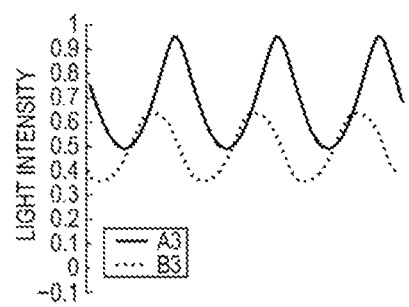
FIG. 9D illustrates intensity distributions of the Moiré relating to Example 3.

If the Fourier transform is performed for the Moiré shown in FIG. 9B, spectra shown in FIG. 9C appear. Like FIG. 4B, a zeroth order spectrum 1204 is present at the center of a wave number space 1203, and first order spectra 1205, 1206, 1207, and 1208 are present around the zeroth order spectrum 1204.

Figure 10:
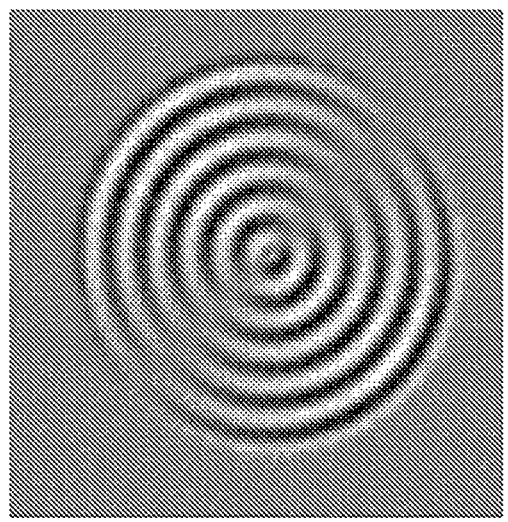
FIG. 10 illustrates the result of wavefront analysis according to Example 3.

FIG. 10 shows the differential phase image obtained in this example.

When the example is compared with the comparative example, since the position of the first order spectrum is obliquely located at 45 degrees, the differential phase image is obliquely inclined at 45 degrees as compared with FIG. 16. Otherwise, jaggies of edges are not noticeable as compared with the differential phase image shown in FIG. 16, and a detailed shape can be reproduced.

FIG. 9D shows intensity distributions of the X-rays along the axes A3 and B3 of the Moiré shown in FIG. 9B. Like the Moiré shown in FIG. 4A, assuming that a direction parallel to the axis A3 is a first direction, the Moiré shown in FIG. 9B provides intensity distributions having an equivalent period in the first direction in the entire region on the Moiré. Accordingly, like Example 1, a detailed shape can be analyzed as compared with the comparative example.

Example 4

In Example 4, an imaging apparatus that uses the same first grating as the first grating in Example 3 will be described with reference to FIGS. 11A to 11D. This example is different from Example 3 in a second grating, and other configuration is the same.

Figure 11A:
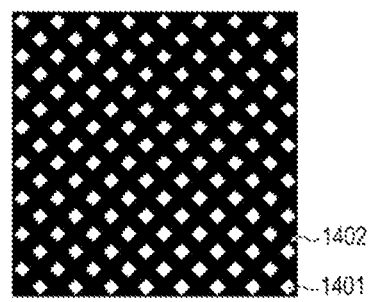
FIG. 11A illustrates a second grating relating to Example 4.

FIG. 11A schematically illustrates part of the second grating in an enlarged manner.

Figure 11B:
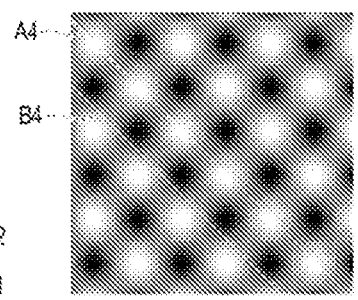
FIG. 11B illustrates a Moiré relating to Example 4.

The second grating used in this example includes transmissive portions 1401 and shielding portions 1402 for X-rays. The transmissive portions 1401 and the shielding portions 1402 are arranged in a lattice-shaped pattern, and are rotated by 45 degrees relative to a self image. The second grating has a period slightly different from the period of the first grating. Due to the difference, a Moiré shown in FIG. 11B is generated. Like Example 1, FIG. 11C illustrates the result obtained by performing the Fourier transform for the Moiré, and FIG. 11D illustrates an intensity distribution of the X-rays along an axis A4 on the Moiré by using a solid line, and an intensity distribution of the X-rays along an axis B4 on the Moiré by using a broken line.

Figure 11C:
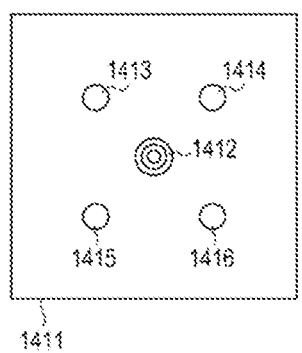
FIG. 11C is a schematic illustration obtained by performing the Fourier transform for the Moiré relating to Example 4.
Figure 11D:
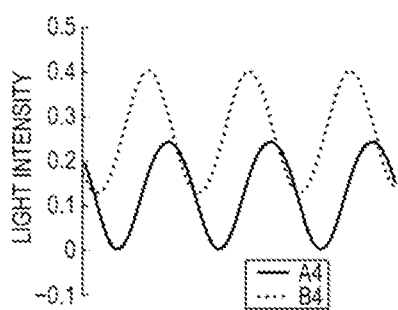
FIG. 11D illustrates intensity distributions of the Moiré relating to Example 4.
Figure 12:
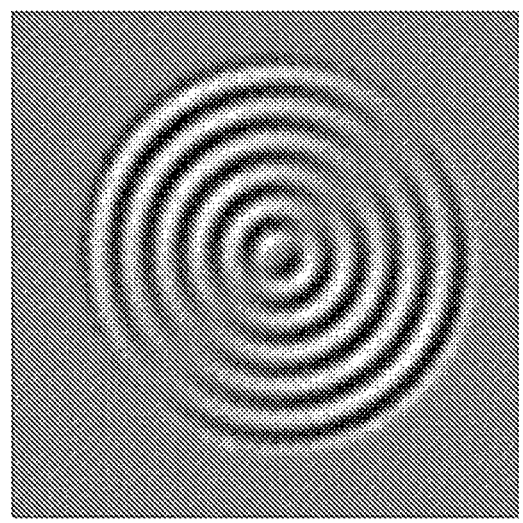
FIG. 12 illustrates the result of wavefront analysis according to Example 4.

If the Fourier transform is performed for the Moiré shown in FIG. 11B, spectra shown in FIG. 11C appear. Like FIG. 4B, in FIG. 11C, a zeroth order spectrum 1412 is present at the center of a wave number space 1411, and first order spectra 1413, 1414, 1415, and 1416 are present around the zeroth order spectrum 1412.

FIG. 10 illustrates a differential phase image obtained in this example.

When the example is compared with the comparative example, since the position of the first order spectrum is obliquely located at 45 degrees, the differential phase image is obliquely inclined at 45 degrees as compared with FIG. 16. Otherwise, jaggies of edges are reduced as compared with the differential phase image shown in FIG. 16, and a smooth curve surface is expressed.

FIG. 11D illustrates intensity distributions of the X-rays along the axes A4 and B4 of the Moiré shown in FIG. 11B. Like the Moiré shown in FIG. 4A, assuming that a direction parallel to the axis A4 is a first direction, the Moiré shown in FIG. 11B provides intensity distributions having an equivalent period in the first direction in the entire region on the Moiré. Accordingly, like Example 1, a detailed shape can be analyzed as compared with the comparative example. Also, the periods of the intensity distributions have shapes that are the most approximate to a sign curve from among the examples. This represents that a high-order spectrum, which serves as a noise as the result of the Fourier transform, hardly appears. In this point of view, Example 4 is more desirable than Examples 1 to 3.

Figure 19A:
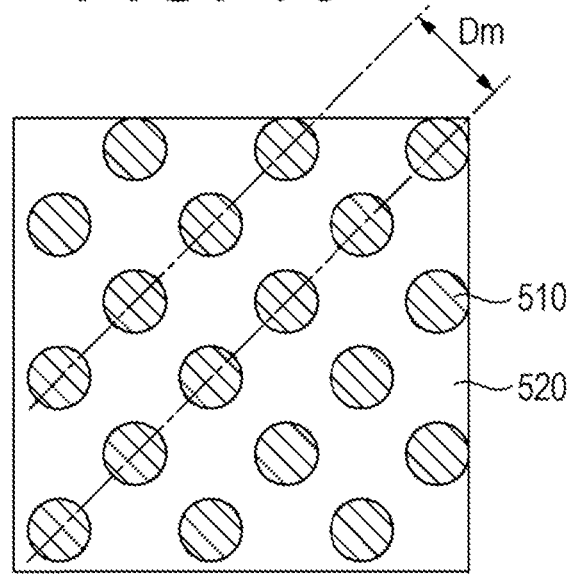
FIGS. 19A illustrates a Moiré relating to the embodiment.
Figure 19B:
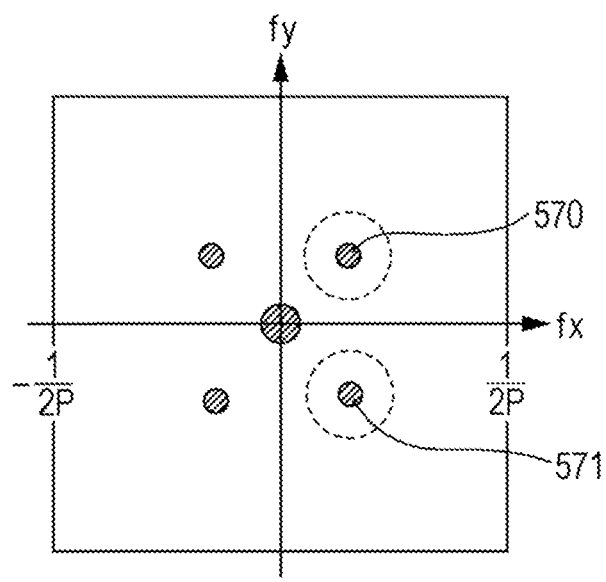
FIG. 19B is a schematic illustration obtained by performing the Fourier transform for the Moiré relating to the embodiment.

FIG. 19A is an example of an intensity distribution of a Moiré when the π/2 phase grating with the checker board designed pattern and the absorption grating with the lattice-shaped pattern (FIG. 18A) or the absorption grating with the checker board designed pattern (FIG. 18B) are used. Reference sign 510 denotes bright sections of the Moiré, and 520 denotes dark sections of the Moiré. It is to be noted that the intensity distribution of the Moiré is generated in an oblique direction even when the π phase grating with the checker board designed pattern (FIG. 17) and the absorption grating with the checker board designed pattern (FIG. 18B) are used. FIG. 19B illustrates spatial frequency spectra acquired by performing processing for the intensity distributions of the Moiré shown in FIG. 19A by fast Fourier transform (FFT) which is a kind of Fourier transform. In FIG. 19B, the peripheries of two peaks 570 and 571, at positions orthogonal to one another, are extracted in a similar manner to the one-dimensional configuration, and are moved to the origin to perform inverse Fourier transform. The extracted regions are indicated by broken lines. By inverse Fourier transform, complex number information is acquired. With the complex number information, differential phase information in the two directions orthogonal to one another is acquired.

Figure 17:
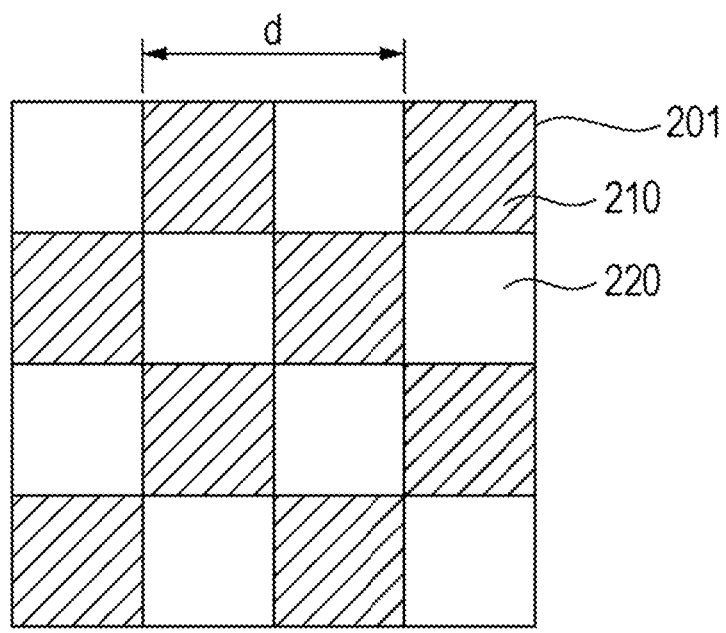
FIG. 17 illustrates a two-dimensional phase gratings relating to the embodiment.

FIG. 17 means a concept of FIG. 2A. In FIG. 17, reference sign d denotes a period, 201 denotes a two-dimensional phase grating, 210 denotes phase advance portions, and 220 denotes phase lag portions. The shape of each phase advance portion 210 or each phase lag portion 220 is a square in FIG. 17. FIG. 18B means a concept of FIG. 3. FIGS. 18A and 18B illustrate an absorption grating 300 with a lattice-shaped pattern, in which transmissive portions 351 and light-shielding portions 352 are two-dimensionally arrayed. For example, if a π phase grating with a checker board designed pattern shown in FIG. 17 is used, an absorption grating 300 with a lattice-shaped pattern, in which transmissive portions 351 and light-shielding portions 352 are two-dimensionally arrayed as shown in FIG. 18, is used. If a π/2 phase grating a checker board designed pattern shown in FIG. 17 is used, an absorption grating 300 with a checker board designed pattern, in which transmissive portions 351 and light-shielding portions 352 are two-dimensionally arrayed as shown in FIG. 18B, is used. FIG. 19A means a concept of FIG. 4A. FIG. 19B means a concept of FIG. 4B.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-278425 filed Oct. 29, 2008, International Patent Application No. PCT/JP2009/068434 filed Oct. 27, 2009, and Japanese Patent Application No. 2010-091562 filed Apr. 12, 2010, which are hereby incorporated by reference herein in their entirety.

What is claimed is:

1. An imaging apparatus comprising:
a first grating configured to form a two-dimensional interference pattern by diffracting light from a light source;
a second grating including two-dimensionally arrayed shielding portions that shield the light and transmissive portions that transmit the light, and configured to shield part of the interference pattern;
a detector configured to detect the light transmitted through the second grating; and
an arithmetic unit configured to calculate a phase image or a differential phase image of a subject based on a periodic pattern of an intensity distribution of the light detected by the detector,
wherein the first and second gratings are configured such that a period of the intensity distribution in a first direction becomes equivalent in an entire region on a detection surface of the detector.

2. The imaging apparatus according to claim 1, wherein the first and second gratins are configured such that a period of the intensity distribution in a second direction that intersects with the first direction becomes equivalent in the entire region on the detection surface of the detector.

3. The imaging apparatus according to claim 1, wherein the first direction perpendicularly intersects with the second direction.

4. The imaging apparatus according to claim 2, wherein the period of the intensity distribution in the first direction and the period of the intensity distribution in the second direction are equivalent.

5. The imaging apparatus according to claim 1, wherein the arithmetic unit analyzes the intensity distribution by using the Fourier transform method.

6. The imaging apparatus according to claim 1,
wherein the arithmetic unit calculates the differential phase image of the subject, and
wherein the first and second directions are differential directions of the differential phase image.

7. The imaging apparatus according to claim 1, wherein the light is X-rays.

8. An imaging apparatus comprising:
a first grating configured to form a two-dimensional interference pattern by diffracting light from a light source;
a second grating including two-dimensionally arrayed shielding portions that shield the light and transmissive portions that transmit the light, and configured to shield part of the interference pattern;
a detector configured to detect the light transmitted through the second grating; and
an arithmetic unit configured to calculate a phase image or a differential phase image of a subject based on a periodic pattern of an intensity distribution of the light detected by the detector,
wherein the interference pattern is a lattice-shaped pattern, and
the shielding portions and the transmissive portions of the second grating are arranged in a checker board designed pattern.

9. An imaging apparatus comprising:
a first grating configured to form a two-dimensional interference pattern by diffracting light from a light source;
a second grating including two-dimensionally arrayed shielding portions that shield the light and transmissive portions that transmit the light, and configured to shield part of the interference pattern;
a detector configured to detect the light transmitted through the second grating; and
an arithmetic unit configured to calculate a phase image or a differential phase image of a subject based on a periodic pattern of an intensity distribution of the light detected by the detector,
wherein the interference pattern is a lattice-shaped pattern,
wherein, in addition to the shielding portions and the transmissive portions, the second grating further includes semi-shielding portions that transmit the light more than the shielding portions do and shield the light more than the transmissive portions do, and
wherein the shielding portions, the transmissive portions, and the semi-shielding portions are respectively arrayed in checker board designed patterns, and are arranged in a Bayer array.

10. An imaging apparatus comprising:
a first grating configured to form a two-dimensional interference pattern by diffracting light from a light source;
a second grating including two-dimensionally arrayed shielding portions that shield the light and transmissive portions that transmit the light, and configured to shield part of the interference pattern;
a detector configured to detect the light transmitted through the second grating; and
an arithmetic unit configured to calculate a phase image or a differential phase image of a subject based on a periodic pattern of an intensity distribution of the light detected by the detector,
wherein the interference pattern is a checker board designed pattern, and
wherein the shielding portions and the transmissive portions of the second grating are arranged in a checker board designed pattern.

11. An imaging apparatus comprising:
a first grating configured to form a two-dimensional interference pattern by diffracting light from a light source;
a second grating including two-dimensionally arrayed shielding portions that shield the light and transmissive portions that transmit the light, and configured to shield part of the interference pattern;
a detector configured to detect the light transmitted through the second grating; and
an arithmetic unit configured to calculate a phase image or a differential phase image of a subject based on a periodic pattern of an intensity distribution of the light detected by the detector,
wherein the interference pattern is a checker board designed pattern, and
wherein the shielding portions and the transmissive portions of the second grating are arranged in a lattice-shaped pattern.

12. An imaging method comprising:
forming a two-dimensional interference pattern by diffracting light by a first grating;
shielding part of the interference pattern by a second grating including two-dimensionally arrayed shielding portions that shield the light and transmissive portions that transmit the light;
detecting the light transmitted through the second grating by a detector; and
analyzing a periodic pattern of an intensity distribution of the light detected by the detector and calculating a phase image or a differential phase image of a subject by an arithmetic unit,
wherein a period of the intensity distribution in a first direction is constant in a detection surface of the detector, and wherein the first and second gratings are configured such that a period of the intensity distribution in a second direction is constant in the detection surface of the detector.

* * * * *